United States Patent
Salters et al.

(10) Patent No.: US 10,668,995 B2
(45) Date of Patent: *Jun. 2, 2020

(54) METHOD AND SYSTEM FOR PREVENTING FOULING OF SURFACES

(71) Applicant: KONINKLIJKE PHILIPS N.V., Eindhoven (NL)

(72) Inventors: Bart Andre Salters, Eindhoven (NL); Roelant Boudewijn Hietbrink, Eindhoven (NL); Ivo Wilhelmus Johannes Marie Rutten, Eindhoven (NL); Hendrik Van Houten, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/477,681

(22) Filed: Apr. 3, 2017

(65) Prior Publication Data

US 2017/0210450 A1 Jul. 27, 2017

Related U.S. Application Data

(63) Continuation of application No. 14/889,155, filed as application No. PCT/IB2014/061579 on May 21, 2014, now Pat. No. 9,611,016.
(Continued)

(30) Foreign Application Priority Data

Nov. 6, 2013 (EP) .................................. 13191713

(51) Int. Cl.
    *B63B 59/04* (2006.01)
    *B08B 17/02* (2006.01)
    (Continued)

(52) U.S. Cl.
    CPC ................. *B63B 59/04* (2013.01); *A61L 2/10* (2013.01); *B08B 7/0057* (2013.01); *B08B 17/02* (2013.01);
    (Continued)

(58) Field of Classification Search
    CPC ......... B63B 59/04; A61L 2/10; B08B 7/0057; B08B 17/02; G02B 6/00; G02B 6/0043;
    (Continued)

(56) References Cited

U.S. PATENT DOCUMENTS 5,050,946 A * 9/1991 Hathaway ................. F21V 7/00
    349/64
5,308,505 A * 5/1994 Titus ..................... A61L 2/0011
    210/745
(Continued)

FOREIGN PATENT DOCUMENTS

JP      5675290 A    6/1981
JP      11278374 A    10/1999
(Continued)

*Primary Examiner* — David E Smith

(57) ABSTRACT

A method of anti-fouling of a surface while said surface is at least partially submersed in an liquid environment, comprising: providing an anti-fouling light; distributing at least part of the light through an optical mediumcomprising a silicone material and/or UV grade fused silica; emitting the anti-fouling light from the optical medium and from the surface.

90 Claims, 10 Drawing Sheets

Related U.S. Application Data

(60) Provisional application No. 61/826,148, filed on May 22, 2013.

(51) Int. Cl.
    *A61L 2/10*     (2006.01)
    *G02B 19/00*     (2006.01)
    *F21V 8/00*     (2006.01)
    *G02B 6/00*     (2006.01)
    *B08B 7/00*     (2006.01)

(52) U.S. Cl.
    CPC .............. *G02B 6/00* (2013.01); *G02B 6/0043* (2013.01); *G02B 19/0019* (2013.01); *G02B 19/0061* (2013.01); *G02B 6/0036* (2013.01)

(58) Field of Classification Search
    CPC ............ G02B 19/0019; G02B 19/0061; G02B 19/0036
    See application file for complete search history.

(56) References Cited

U.S. PATENT DOCUMENTS

| | | | |
|---|---|---|---|
| 6,094,767 A | 8/2000 | Iimura | |
| 9,611,016 B2* | 4/2017 | Salters | B08B 17/02 |
| 9,776,219 B2* | 10/2017 | Whelan | B63B 59/04 |
| 9,910,202 B2 | 3/2018 | Ahn et al. | |
| 2009/0129115 A1* | 5/2009 | Fine | G02B 6/0021 |
| | | | 362/606 |
| 2010/0199906 A1* | 8/2010 | Stieglitz | A01K 79/02 |
| | | | 114/219 |
| 2011/0226966 A1* | 9/2011 | Takahashi | A01K 63/04 |
| | | | 250/492.1 |
| 2012/0050520 A1 | 3/2012 | Thoren | |
| 2012/0069579 A1 | 3/2012 | Koh et al. | |
| 2013/0048877 A1* | 2/2013 | Thoren | G02B 6/102 |
| | | | 250/492.1 |
| 2013/0114292 A1* | 5/2013 | Brick | G02B 6/0041 |
| | | | 362/608 |
| 2014/0202962 A1* | 7/2014 | Bilenko | C02F 1/325 |
| | | | 210/748.11 |

FOREIGN PATENT DOCUMENTS

| | | |
|---|---|---|
| JP | 2011126248 A | 6/2011 |
| JP | 2012043630 A | 3/2012 |
| JP | 2012252217 A | 12/2012 |
| WO | 9800964 A2 | 1/1998 |
| WO | 2007087710 A1 | 8/2007 |
| WO | 2007107722 A1 | 9/2007 |

\* cited by examiner

METHOD AND SYSTEM FOR PREVENTING FOULING OF SURFACES

CLAIM OF PRIORITY

This application claims, pursuant to 35 USC 120, as a Continuation, priority to and the benefit of the earlier filing date of that patent application filed on Nov. 5, 2015 and afforded Ser. No. 14/889,155, which filed claimed as a National Stage filing of PCT/IB2014/061579 filed on May 21, 2014, which claimed, priority to and the benefit of the earlier filing date of provisional patent application filed on May 22, 2013 and afforded Ser. No. 61/826,148, the contents of all of which are incorporated by reference, herein.

TECHNICAL FIELD

The present disclosure relates to methods for preventing fouling, or commonly referred to as anti-fouling, of surfaces and to devices for performing these methods. The disclosure specifically relates to methods and devices for anti-fouling of the hull of ships.

BACKGROUND

Biofouling or biological fouling is the accumulation of microorganisms, plants, algae, and/or animals on surfaces. The variety among biofouling organisms is highly diverse and extends far beyond attachment of barnacles and seaweeds. According to some estimates, over 1700 species comprising over 4000 organisms are responsible for biofouling. Biofouling is divided into microfouling which includes biofilm formation and bacterial adhesion, and macrofouling which is the attachment of larger organisms. Due to the distinct chemistry and biology that determine what prevents organisms from settling, these organisms are also classified as hard or soft fouling types. Calcareous (hard) fouling organisms include barnacles, encrusting bryozoans, mollusks, polychaete and other tube worms, and zebra mussels. Examples of non-calcareous (soft) fouling organisms are seaweed, hydroids, algae and biofilm "slime". Together, these organisms form a fouling community.

In several circumstances biofouling creates substantial problems. Machinery stops working, water inlets get clogged, and hulls of ships suffer from increased drag. Hence the topic of anti-fouling, i.e. the process of removing or preventing fouling from forming, is well known. In industrial processes, bio-dispersants can be used to control biofouling. In less controlled environments, organisms are killed or repelled with coatings using biocides, thermal treatments or pulses of energy. Nontoxic mechanical strategies that prevent organisms from attaching include choosing a material or coating with a slippery surface, or creation of nanoscale surface topologies similar to the skin of sharks and dolphins which only offer poor anchor points.

SUMMARY

Biofouling on the hull of ships, as illustrated in FIG. 1, causes a severe increase in drag, and thus increased fuel consumption. It is estimated that an increase of up to 40% in fuel consumption can be attributed to biofouling. As large oil tankers or container transport ships can consume up to €200.000 a day in fuel, substantial savings are possible with an effective method of anti-biofouling.

Herewith an approach is presented based on optical methods, in particular using ultra-violet light (UV). It is well-known that most micro-organisms are killed, rendered inactive or unable to reproduce with 'sufficient' UV light. This effect is mainly governed by the total dose of UV light. A typical dose to kill 90% of a certain micro-organism is 10 mW-hours per square meter, details are contained in the following paragraphs regarding UV light, and the associated Figures.

Ultraviolet Light in General

Ultraviolet (UV) is that part of electromagnetic light bounded by the lower wavelength extreme of the visible spectrum and the X-ray radiation band. The spectral range of UV light is, by definition between 100 and 400 nm (1 nm=$10^{-9}$ m) and is invisible to human eyes. Using the CIE classification the UV spectrum is subdivided into three bands:

UVA (long-wave) from 315 to 400 nm
UVB (medium-wave) from 280 to 315 nm
UVC (short-wave) from 100 to 280 nm In reality many photobiologists often speak of skin effects resulting from UV exposure as the weighted effect of wavelength above and below 320 nm, hence offering an alternative definition.

A strong germicidal effect is provided by the light in the short-wave UVC band. In addition erythema (reddening of the skin) and conjunctivitis (inflammation of the mucous membranes of the eye) can also be caused by this form of light. Because of this, when germicidal UV-light lamps are used, it is important to design systems to exclude UVC leakage and so avoid these effects. In case of immersed light sources, absorption of UV light by water may be strong enough that UVC leaking is no problem for humans above the liquid surface.

Self evidently people should avoid exposure to UVC. Fortunately this is relatively simple, because it is absorbed by most products, and even standard flat glass absorbs substantially all UVC. Exceptions are e.g. quartz and PTFE (PolyTetraFluorEth(yl)ene). Again fortuitously, UVC is mostly absorbed by dead skin, so erythema can be limited. In addition UVC does not penetrate the eye's lens; nevertheless, conjunctivitis can occur and though temporary, it is extremely painful; the same is true of erythemal effects.

Where exposure to UVC light occurs, care should be taken not to exceed the threshold level norm. FIG. 2 shows these values for most of the CIE UV spectrum. In practical terms, Table 1 gives the American Congress of Governmental and Industrial Hygienist's (ACGIH) UV Threshold Limit Effective Irradiance Values for human exposure related to time. At this time it is worth noting that radiation wavelengths below 240 nm forms ozone, $O_3$, from oxygen in air. Ozone is toxic and highly reactive; hence precautions have to be taken to avoid exposure to humans and certain materials.

TABLE 1 permissible UVC exposures for humans according to ACGIH

| Duration of exposure per day | Irradiance ($\mu W/cm^2$) |
|---|---|
| 8 hours | 0.2 |
| 4 hours | 0.4 |
| 2 hours | 0.8 |
| 1 hour | 1.7 |
| 30 minutes | 3.3 |
| 15 minutes | 6.6 |
| 10 minutes | 10 |
| 5 minutes | 20 |
| 1 minute | 100 |

Generation and Characteristics of Short-Wave UV Light

The most efficient source for generating UVC is the low-pressure mercury discharge lamp, where on average 35% of input watts is converted to UVC watts. The radiation is generated almost exclusively at 254 nm viz. at 85% of the maximum germicidal effect (FIG. 3). Philips' low pressure tubular flourescent ultraviolet (TUV) lamps have an envelope of special glass that filters out ozone-forming radiation, in this case the 185 nm mercury line. The spectral transmission of this glass is shown in FIG. 4 and the spectral power distribution of these TUV lamps is given in FIG. 5.

For various Philips germicidal TUV lamps the electrical and mechanical properties are identical to their lighting equivalents for visible light. This allows them to be operated in the same way i.e. using an electronic or magnetic ballast/starter circuit. As with all low pressure lamps, there is a relationship between lamp operating temperature and output. In low pressure lamps the resonance line at 254 nm is strongest at a certain mercury vapour pressure in the discharge tube. This pressure is determined by the operating temperature and optimises at a tube wall temperature of 40° C., corresponding with an ambient temperature of about 25° C. It should also be recognised that lamp output is affected by air currents (forced or natural) across the lamp, the so called chill factor. The reader should note that, for some lamps, increasing the air flow and/or decreasing the temperature can increase the germicidal output. This is met in high output (HO) lamps viz. lamps with higher wattage than normal for their linear dimension.

A second type of UV source is the medium pressure mercury lamp, here the higher pressure excites more energy levels producing more spectral lines and a continuum (re-combined radiation) (FIG. 6). It should be noted that the quartz envelope transmits below 240 nm so ozone can be formed from air. Advantages of medium pressure sources are:
high power density;
high power, resulting in fewer lamps than low pressure types being used in the same application; and
less sensitivity to environment temperature.

The lamps should be operated so that the wall temperature lies between 600 and 900° C. and the pinch does not exceed 350° C. These lamps can be dimmed, as can low pressure lamps.

Further, Dielectric Barrier Discharge (DBD) lamps can be used. These lamps can provide very powerful UV light at various wavelengths and at high electrical-to-optical power efficiencies.

The germicidal doses listed above can also easily be achieved with existing low cost, lower power UV LEDs. LEDs can generally be included in relatively smaller packages and consume less power than other types of light sources. LEDs can be manufactured to emit (UV) light of various desired wavelengths and their operating parameters, most notably the output power, can be controlled to a high degree.

An basic idea underlying the present disclosure is to cover significant amounts of a protected surface to be kept clean from fouling, preferably the entire protected surface, e.g. the hull of a ship, with a layer that emits germicidal light, in particular UV light.

Accordingly, herewith a method of anti-fouling of a protected surface as well as a lighting module and a system for anti-fouling of a protected surface according to the appended claims are provided.

A method comprises providing anti-fouling light and emitting the anti-fouling light in a direction away from a protected surface, wherein at least part of the light is distributed across a substantial part of the protected surface by an optical mediumbefore being emitted in the direction away from the protected surface. In embodiments, the method comprises emitting the anti-fouling light from a substantially planar emission surface of the optical medium. In embodiments the method uses a light guide to distribute the light across a substantial part of the protected surface and comprises silicone material and/or UV grade silica material, in particular quartz. The method is preferably executed while the protected surface is at least partially submersed in a liquid environment.

A lighting module for anti-fouling of a protected surface comprises at least one light source for generating anti-fouling light and an optical medium for distributing the anti-fouling light from the light source. The at least one light source and/or the optical medium may be at least partly arranged in, on and/or near the protected surface so as to emit the anti-fouling light in a direction away from the protected surface. The lighting module is adapted to preferably emit the anti-fouling light while the protected surface is at least partially submersed in an liquid environment. In an embodiment, the optical medium is a light guide comprises a silicone material and/or UV grade silica material.

The lighting module for anti-fouling of a protected surface may also be provided as a foil for applying to the protected surface, the foil comprising at least one light source for generating anti-fouling light and a sheet-like optical medium for distributing the anti-fouling light across the foil. In embodiments the foil has a thickness in an order of magnitude of a couple of millimeters to a few centimeters. In embodiments, the foil is not substantially limited in any direction perpendicular to the thickness direction so as to provide substantially large foil having sizes in the order of magnitude of tens or hundreds of square meters. The foil may be substantially size-limited in two orthogonal directions perpendicular to the thickness direction of the foil, so as to provide an anti-fouling tile; in another embodiment the foil is substantially size-limited in only one one direction perpendicular to a thickness direction of the foil, so as to provide an elongated strip of anti-fouling foil.

The lighting module, whether arranged in, on and/or near the protected surface or whether provided as a separate foil, comprises an emission surface for emitting the anti-fouling light from the optical medium into an evironment and a application surface, opposed the emission surface, for applying or arranging the lighting module to the protected surface. In a preferred embodiment the emission surface of the light module is substantially planar so as to avoid pits and indent which may become seeds of fouling and so as to avoid bulges to limit the amount of drag caused by the structure when applied to the protected surface. The advantage of a substantially planar surface versus a surface comprising indents and bulges or having a substantial surface roughness is that it will be more difficult for mircoorganisms to adhere to a substantiall plane surface, especially in combination with drag effects in a liquid environment, than they would onto a rough surface or into pits comprises in said surface. The term 'substantially planar' emission surface herein refers to a surface masking or obscuring the thickness of light sources and wiring connections embed in or attached to the lighting module. The term 'substantially planar' may also refer to masking or obscuring some constructional uneveness of the protected surface, thereby even improving the drag properties of the protected surface in the liquid environment. Example of constructional uneveness of the protected surface are welds, rivets, etc. The term 'substantially planar' can be quantified as resulting in variations in the average thickness of the light modules of less than 25%, preferably less than 10%. 'Substantially planar' therefore not necessarily requires a surface roughness of a machined surface finish.

In a preferred embodiment the lighting module comprises a two-dimensional grid of light sources for generating anti-fouling light and the optical medium is arranged to distribute at least part of the anti-fouling light from the two-dimensional grid of light sources across the optical medium so as to provide a two-dimensional distribution of anti-fouling light exiting the light emitting surface of the light module. The two-dimensional grid of light sources may be arranged in a chickenwire structure, a close-packed structure, a rows/columns structure, or any other suitable regular or irregular structure. The physical distance between neigboring light sources in the grid may be fixed across the grid or may vary, for example as a function of light output power required to provide the anit-fouling effect or as function of the location of the lighting module on the protected surface (e.g location on the hull of a ship). Advantages of providing a two-dimensional grid of light sources include that the anti-fouling light may be generated close to the areas to be protected with anti-fouling light illumination, and that it reduced losses in the optical medium or light guide and that is increasing homogeneity of the light distribution. Preferably, the anti-fouling light is generally homogeneously distributed across the emission surface; this reduces or even prevents under-illuminated areas, where fouling may otherwise take place, while at the same time reducing or preventing energy waste by over-illumination of other areas with more light than needed for anti-fouling.

In preferred embodiments, the light sources are UV LEDs. The at least one UV LED or the grid of UV LEDs may be encapsulated in a liquid-tight encapsulation. In embodiments the at least one UV LED or the grid of UV LEDs may be embedded in the optical medium. A plurality of UV LEDs may be organised in grid and electrically connected in a series/parallel chicken-wire structure (as will be explained later). The LEDs and the chicken-wire connections may be encapsulated in a light-transmissive coating and attached to the optical medium or directly embed in the optical medium. In other embodiments the grid of UV LEDs may be comprised in a layer of electronic textile which is embedded in a resin structure. In some embodiments the UV LEDs may be packaged LEDs, in which case they already may include an optical element to distribute the light emitted from the LED package across a wide emission angle. In other embodiment the UV LEDs may be LED dies, typically not comprising optical elements but being significantly thinner than packaged LEDs. As an example, LED dies could be picked and placed onto a surface of the optical medium (preferably the application surface, but the emission surface would do as well because of the small size of the components which will nearly not interfering with the light emission function of said surface), electrical wired via printing of conductive paste and finally the LED dies and wiring could be encapsulated with a thin layer/coating of the optical medium or any other backing layer for applying the lighting module to the protected surface. Various embodiments of embedded light sources allow the presented anti-fouling technology to be commercialized as a foil for applying on the hull of ships.

A system for anti-fouling of a protected surface may comprise a plurality of lighting modules as disclosed herein for arranging on the protected surface so as to provide anti-fouling light over substantially the entire area of the protected surface.

Silicone materials can provide optical transmission for UV light with little loss compared to other materials. This is in particular the case for shorter wavelength light, e.g. UV light with wavelengths below 300 nm. A particularly efficient group of silicone materials is, or at least comprises, so-called methyl silicones, according to the general chemical formula $CH_3[Si(CH_3)_2O]_nSi(CH_3)_3$, with "n" indicating any suitable integral, as customary in organic chemistry. This type of silicone materials happens to exhibit excellent UV transmission properties with little losses, at least compared to other silicone materials. Further, silicone materials are flexible and resilient so that they are robust, durable and capable of withstanding compression such as due to bumps, collisions etc of objects against the surface, e.g. bumping of a ship against a quai. Further, deformation of a ship's skin due to temperature fluctuation, pounding by waves, ship's flexion over swell and heave etc may be accommodated. Also, silicone materials can be applied and formed over surface structures: welds, rivets, etc. in or on the surface. Silicone materials also tend to adhere well to metals and paints so that a protective coating over the surface is formed. Visibly transparent silicone materials enable reading of underlaying markings (e.g. painted symbols) covered by the silicone material. Further, they are generally water repellent and may reduce friction and drag. On the one hand silicones can be made very smooth to reduce adherence of biofouling organisms to the layer and to reduce friction against flowing water, while on the other hand the material may be finely structured so as to mimic shark's skin which is also known to reduce friction in water at sufficient speed relative to the surrounding water. It is noted that a structured surface of an optical medium, in particular a light guide, can cause breaking conditions for total internal reflection and therewith cause coupling out of light from the light guide that was otherwise captured within and transmitted with total internal reflection. Thus, coupling out of light can be localised reliably.

UV grade silica has very low absorption for UV light and thus is very well suitable as optical medium and light guide material. Relatively large objects may be made from using plural relatively small pieces or portions of UV grade silica together and/or so-called "fused silica", while retaining the UV-transmissive properties also for the larger object. Silica portions embedded in silicone material protect the silica material. In such combination the silica portions may provide UV transparent scatterers in an otherwise silicone material optical medium for (re-)distribution of the light trough the optical medium and/or for facilitating outcoupling of the light from a light guide. Also, silica particles and/or particles of other hard, UV translucent material may fortify the silicone material. In particular flake-shaped silica particles may be used, also in high density, of up to 50%, 70% or even higher percentages of silica in silicone material may provides a strong layer that can resist impacts. It is considered that at least a part of the optical medoum or light guide may be provided with a spatially varying density of UV grade silica particles, in particular flakes, at least partly embedded in a silicone material, e.g. to vary optical and/or structural properties. Here, "flakes" denote objects having sizes in three cartesian directions, wherein two of the three sizes may mutually differ, however, each being significantly larger, e.g. a factor 10, 20, or significantly more, e.g. factors of 100's, than the third size.

In embodiments, in parts of the optical medium close to the emission surface for emitting the anti-fouling light from the optical medium, the density of the UV grade silica particles in the silicone material may increase from within the optical medium towards the emission surface of the optical medium, so that at or near the emission surface a relatively high density of silica particles is provided. Although more or less spherical and/or random-shaped particles may be used, silica flakes of sub-millimeter length scales, e.g. with typical sizes down to a few micrometers, may be arranged so close together that under the influence of very local forces, such as a point-impacts from sharp-tipped objects, and/or localised impacts from blunt objects, including scratches, tears etc, the flakes may have some, if only little, freedom of movement in the flexible silicone that they can slightly rearrange themselves, dissipating the impact energy and reducing damage to the light guide as a whole. Thus, a balance of properties can be struck that results in both a robust and a somewhat deformable layer, yet also providing the desired optical qualities. In an embodiment the proportion of silicone material in the optical medium varies gradually from about 100% (i.e. substantially pure silicone material) to below about 5% (mostly silica) from one side of the optical medium to an opposite side.

It is noted that particles, in particular flake-shaped particles, of other material than silica may be used, e.g. glass or mica. Such other materials may also serve as scatterers for the anti-fouling light. Mixtures of particles of different materials may also be provided, which may comprise mixtures of translucent, opaque and/or optically active particles. Compositions of such mixtures may vary across the light guide, e.g. to adjust transmittivity of the light guide for the anti-fouling light, in particular if in some portions relatively large amounts of poorly-transmitting particles are used.

For manufacturing the optical medium, a series of layers of silicone material may be formed, each possibly having a different composition with regard to the amount and/or density of silica particles. The layers may be very thin and at least some may be applied with a wet-on-wet technique, i.e. providing the silicone material to the layer in liquid or gelatinous form that should harden to the desired layer, but wherein a subsequent layer is applied to an earlier layer before the earlier layer has fully hardened. Thus, a good adhesion between the layers is promoted and in the final product different layers may be hardly to not discernible and a gradual change in composition may be achieved. Different layers may suitably be formed and/or applied by spraying of the layer material. A layered material may be formed to any suitable thickness with good quality control. Note that the optical medium, which consitutes a substantial part of the lighting module's surface, may be attached to the protected surface in any suitable way, including gluing. Silicone materials tend to exhibit strong adhesion to ceramic, glassy and metallic materials and spraying or smearing silicone material is therefore a very suitable manner of forming and attaching the optical medium to a substrate. A sprayed and/or smeared optical medium can also readily be made in different desired shapes, e.g. following a water line, specific markings and/or surface shapes. A layering technique may also facilitate orienting particles in the silicone material, e.g. arranging flakes generally parallel to the direction of expansion of the layer and the surface coated with the layer.

In another aspect of the lighting module, the optical medium comprises spaces, e.g. channels which are filled with gas and/or clear liquid, e.g. water, for guiding the light therethrough and an associated method comprises distributing at least part of the light through such spaces in an optical medium. It is found that optical transmission for UV light through gaseous matter, in particular air, is generally significantly better than transmission of the light through a solid material which may, even if found translucent or transparent by some, exhibit absorption losses of up to several percents per millimeter. Clear liquid provides little scattering, may well transport UV light and may also provide structural robustness of cavities in the optical medium compared to filling the spaces with gas. Water, most notably fresh water, has been found to have a relatively high and suitable UV transmittivity. Contamination and/or UV absorption may be also and/or further reduced if distilled, deionised and/or otherwise purified water is used. Hence, it is considered particularly beneficial to transmit the light through a gas- and/or liquid-filled space. For distribution of the light across the protected surface, the gas- and/or liquid-filled space should preferably be well defined and channels may be provided in a optical medium. Light that eventually strikes walls of the channels can enter the optical medium and be emitted from the optical medium in a direction from the protected surface and into the liquid environment to provide the anti-fouling light. An optical medium in which the air channels are defined that is itself well transparent to the anti-fouling light further assures that if the optical medium would leak and the liquid medium enters the optical medium, generated anti-fouling light would still be appropriately transmitted through the optical medium. Channels may comprise varying diameter. Localised channel portions or pockets may be provided by wall portions defining and encapsulating separate volumes (much) bigger than the respective wall portions' sizes and/or thicknesses, e.g. similar to the packaging product sold under the brand name "Bubble Wrap".

In a particular embodiment, such gas-containing optical medium comprises a silicone material defining the gas and/or liquid-filled channels and/or other spaces; silicone materials may well be shaped to define intricate structures. Further advantages of silicone materials, with or without additional objects such as silica particles have been set out above.

In an embodiment, the channels and/or other spaces are provided by forming two opposing layers of silicone material kept separated at desired distances with wall portions and/or pillars of silicone material creating a distance, e.g. an air gap between the layers. Such wall portions and/or pillars may serve as scattering centres for (re-)distributing the light through (the channels in) the optical medium and/or for guiding light from the gas- and/or liquid filled space(s) into the silicone material. This facilitates localising emission of the light from the optical medium into the liquid environment where the anti-fouling light is to be put to use.

At least part of the anti-fouling light emitted by the one or more light sources may be spread in a direction having a component substantially parallel to the protected surface, or substantially parallel to the application surface of the foil when the light moduled is provided as a foil. This facilitates distributing the light over significant distances along the protected surface, or the application surface of the foil, which assists in obtaining a suitable intensity distribution of the anti-fouling light.

A wavelength conversion material may be comprised in the optical medium and at least part of the anti-fouling light may be generated by photo-exciting the wavelength conversion material with light having a first wavelength causing the wavelength conversion material to emit the anti-fouling light at another wavelength. The wavelength conversion material may be provided as an upconversion phosphor, quantum dots, nonlinear media such as one or more photonic crystal fibers etc. Since absorption and/or scattering losses in the optical medium for light of different, mostly longer, wavelengths than UV light tend to be less pronounced in optical media, it may be more energy-efficient to generate non-UV light and transmit that through the optical medium and to generate UV anti-fouling light at or near the desired location of use thereof (i.e. emission form the surface into the liquid environment). Also, or alternatively, the at least one light source may comprise at least one of an LED or OLED, a DBD lamp and/or a metal vapour lamp (e.g. low pressure mercury vapour lamp). Suitable anti-fouling light is in the wavelength range of UV or blue light from about 220 nm to about 420 nm, in particular at wavelengths shorter than about 300 nm, e.g. from about 240 nm to about 280 nm.

In embodiments, the optical medium comprises a light spreader arranged in front of the at least one light source for generating anit-fouling light for spreading at least part of the anti-fouling light emitted by the at least one light source in a direction having a component substantially parallel to the protected surface. An example of a light spreader may be a 'opposite' cone arranged in the optical medium and position opposite the at least one light source, where the opposite cone has a surface area with a 45° angle perpendicular to the protected surface for reflecting light emitted by the light source perpendicular to said surface in an a direction substantially parallel to said surface. In embodiments the optical medium comprises a light guide arranged in front of the at least one light source for generating the anti-fouling light, the light guide having a light coupling-in surface for coupling in the anti-fouling light from the at least one light source and a light coupling-out surface for coupling-out the anti-fouling light in a direction away from the protected surface; the light guide comprising a light guide material having a refractive index higher than the refractive index of the liquid environment such that at least part of the anti-fouling light is propagated through the light guide via total internal reflection in a direction substantially parallel to the protected surface before being out-coupled at the out-coupling surface. Some embodiment may comprise an optical medium which combines a light spreader and a light guide, or integrated light spreading features with light guiding features into the optical medium. In embodiments, the light spreader and/or light guide is coated onto the protected surface. In other embodiments, the light spreader and/or light guide is provided in the form factor of a foil for applying onto a protected surface.

An embodiment of a system for preventing fouling may comprise:
  a series of UV LEDs for generating anti-fouling light;
  a light spreader for spreading the anti-fouling light from the LED point sources across the protected surface; and
  a light guide for further guiding/spreading the anti-fouling light can be spread across the surface, the light guide comprising a tin layer of silicone material transparent to UV light, with or without silica particles or one or more silica coverered portions.

When substantially the entire protected surface is covered with an anti-fouling light emitting optical medium, it substantially reduces the growth of micro-organisms on this medium. As the micro-organisms are killed on the emission surface of the optical medium, the hull is continuously cleaned through the water flow along the hull which transports the debris away from the ship and micro-organisms do not stand a chance of fouling on the hull.

It is an advantage of the presently provided solutions that the micro-organisms are not killed after having adhered and rooted on the fouling surface, as is the case for known poison dispersing coatings, but that the rooting of micro-organisms on the fouling surface is prevented. It is more efficient to actively kill micro-organism right before or just after they contact the fouling surface, compared to a light treatment to remove existing fouling with large micro-organism structures. The effect may be similar to the effect created by using nano-surfaces that are that smooth that micro-organism cannot adhere to it.

Because the low amount of light energy required for killing the micro-organism in the initial rooting stage, the system may be operated to continuously provide an anti-fouling light across a large surface without extreme power requirements.

A grid of LEDs creating a lighting surface may be provided with energy harvesting means such as for example embedded solar cells, small turbines operating in the water, piezoelectric elements operating on pressure waves, etc.

Some advantages of the presently provided technology include the retention of clean surface, Reduction of the cost of corrosion treatment, reduced fuel consumption for ships, reduced maintenance time for hulls, educed $CO_2$ emission, reduce the use of toxic substances in the environment, etc. A substantially planar and smooth light emission surface further has the advantage of not adding drag by itself and can even further reducing drag by burying existing uneveness (rivets, welds, etc.) of the protected surface underneath the optical medium.

The features disclosed in the context of a lighting module described in the present disclosure may also have a corresponding process step in the method for anti-fouling of a protected surface and vice versa, without explicitly being mentioned in the description. Corresponding features will generally produce the same technical effect.

The disclosed method and lighting module can be applied to prevent fouling on hulls of ships, but they are applicable to all marine objects including stationary (pipes, marine stations etc.) and/or moving marine objects (submarines etc.). The disclosed anti-fouling solution may also be applied to objects operating in waterways, canals or lakes and for example also to aquariums.

DETAILED DESCRIPTION OF EMBODIMENTS

Figure 1:
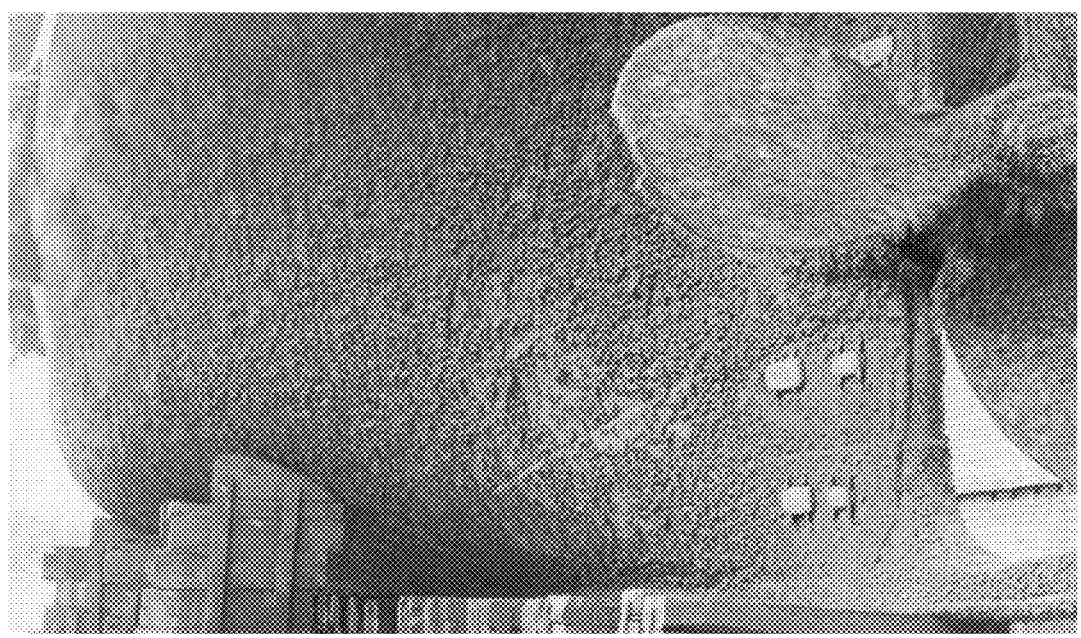
FIG. 1 shows a ships hull suffering from fouling.
Figure 2:
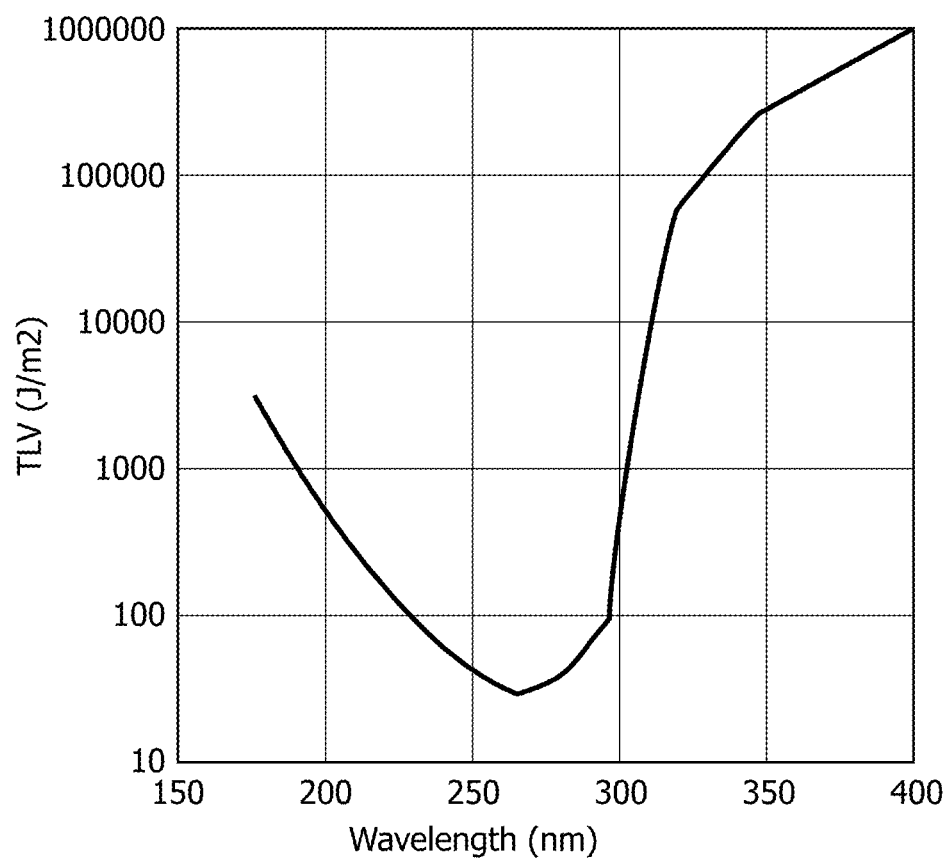
FIG. 2 is a graph showing UV Light Threshold Limited Values (TLV) according to the American Congress of Governmental and Industrial Hygienist's (ACGIH)
Figure 3:
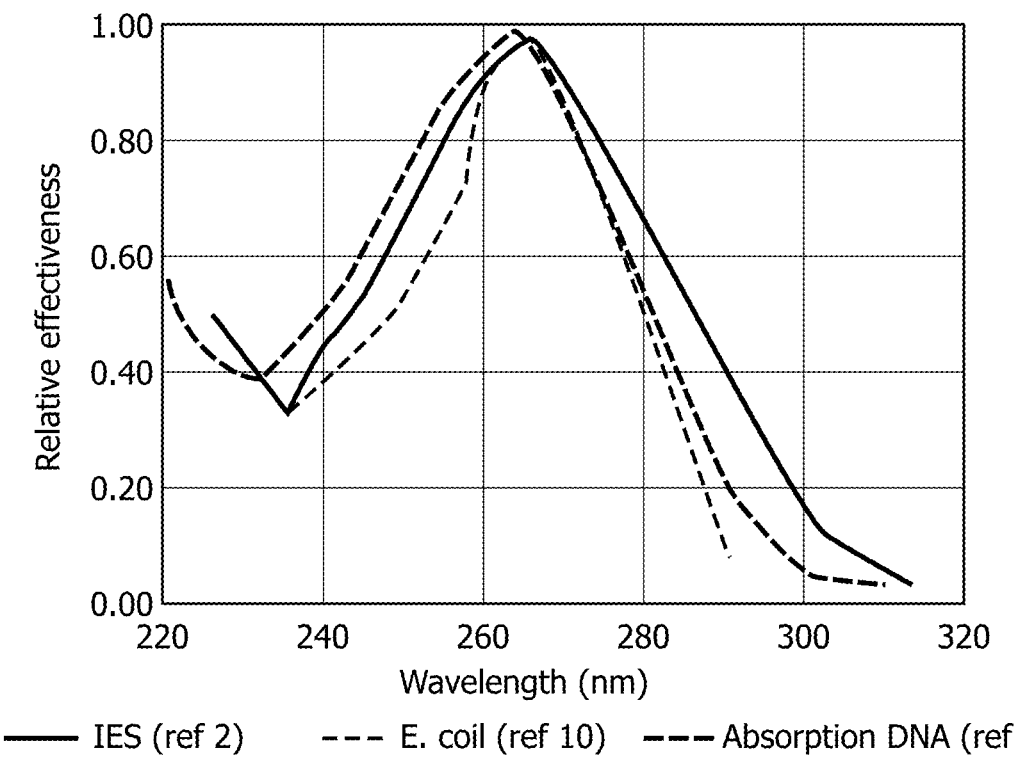
FIG. 3 is a graph showing a germicidal action spectrum for different biological materials as a function of light wavelength.
Figure 4:
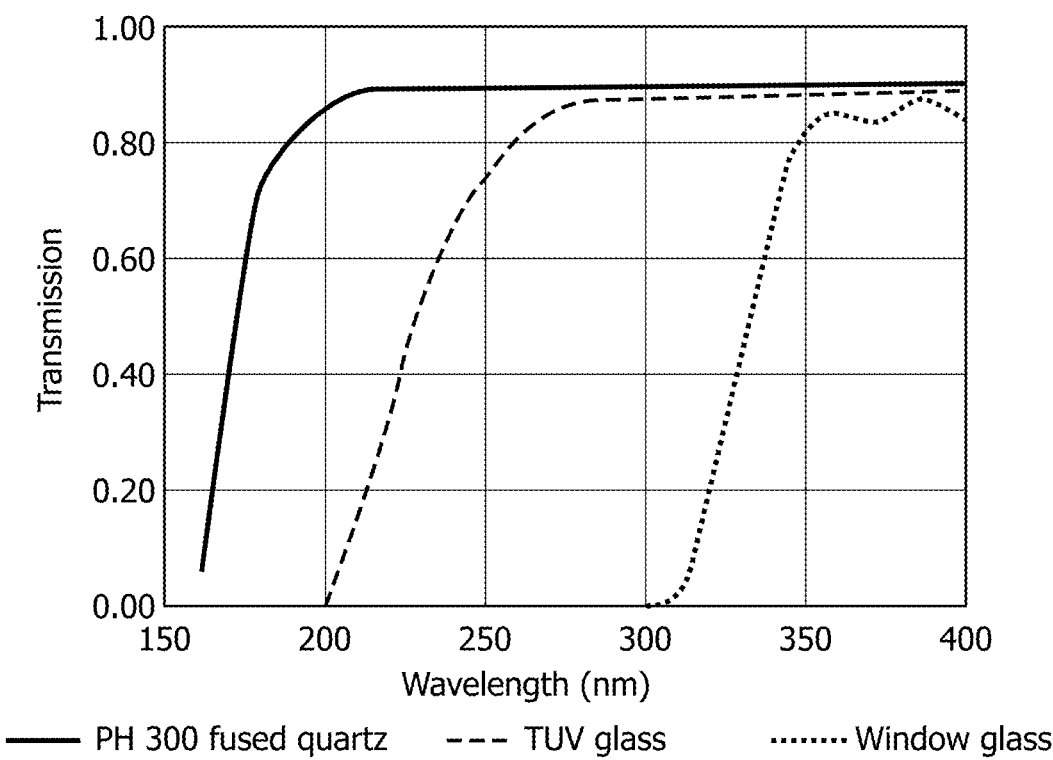
FIG. 4 is a graph showing a transmission spectrum for different types of glass.
Figure 5:
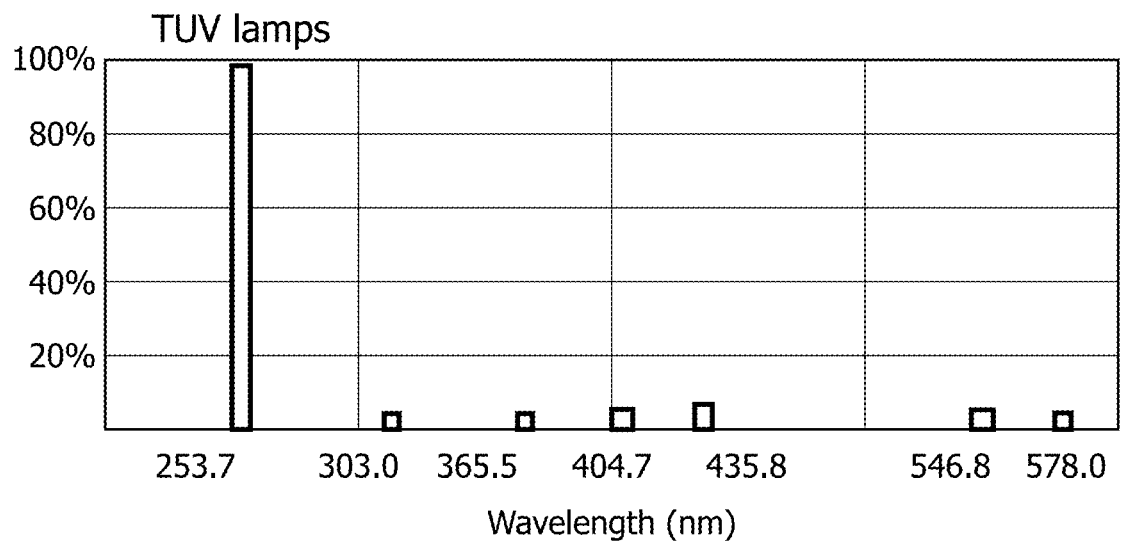
FIG. 5 is a bar graph showing the relative spectral power distribution of typical Philips low pressure tubular fluorescent ultraviolet (TUV) lamps.
Figure 6:
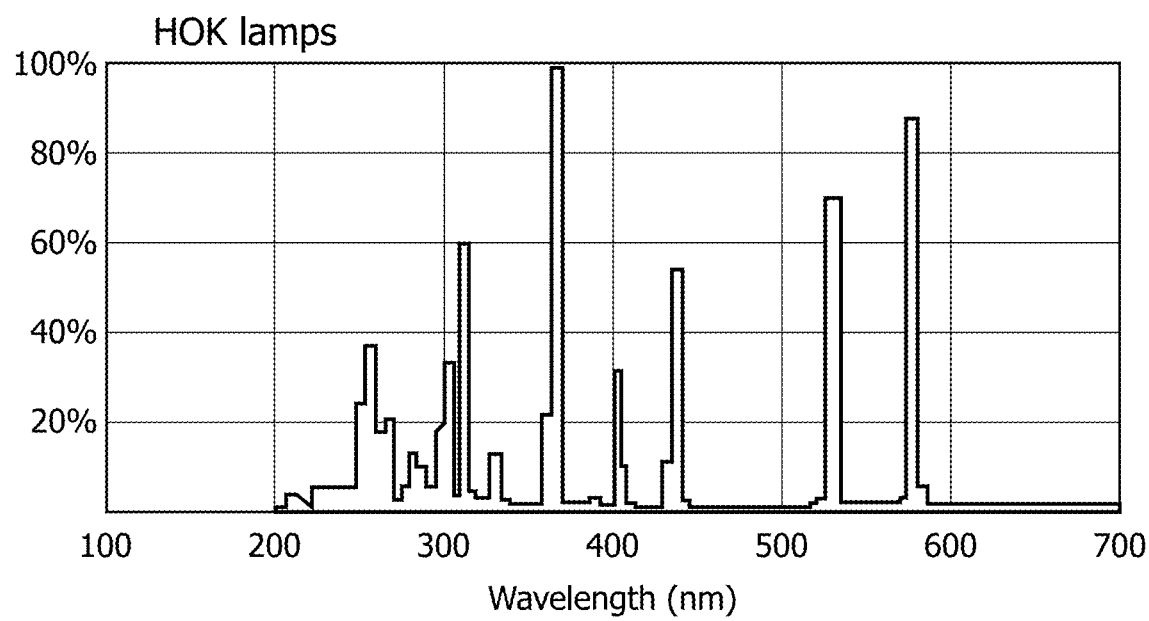
FIG. 6 is a bar graph showing the relative spectral power distribution of Philips medium pressure discharge lamps (HOK and HTK types)

While the disclosure has been illustrated and described in detail in the drawings and foregoing description, such illustration and description are to be considered illustrative or exemplary and not restrictive; the disclosure is not limited to the disclosed embodiments. It is further noted that the drawings are schematic, not necessarily to scale and that details that are not required for understanding the present invention may have been omitted. The terms "upward", "downward", "below", "above", and the like relate to the embodiments as oriented in the drawings, unless otherwise specified. Further, elements that are at least substantially identical or that perform an at least substantially identical function are denoted by the same numeral.

Figure 7:
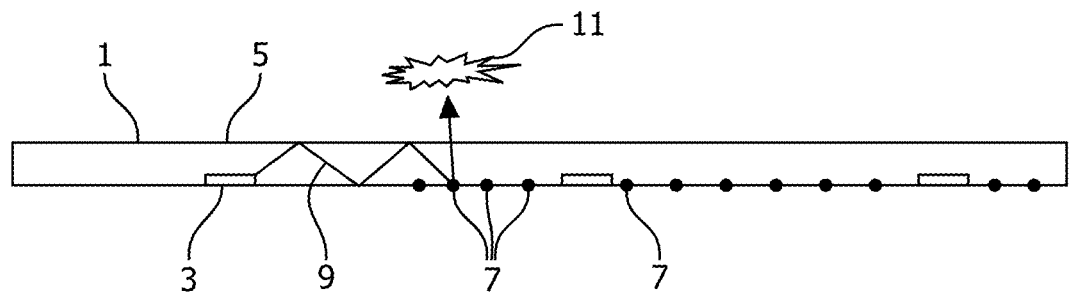
FIG. 7 is a schematic cross section view of a light module with a light guide.

FIG. 7 shows as a basic embodiment a cross section of a lighting module 1 comprising a plurality of light sources 3 (here: side-emitting LEDs, wherein the light is emitted primarily from the side of the LED, and more or less parallel to the surface) encapsulated in a liquid-tight optical medium 5 to guide at least part of the light 9 emitted from the light sources 5 via total internal reflection through the optical medium, which optical medium is further provided with optical structures 7 to scatter light 9 and guide the light 9 out of the optical medium 5 towards an object 11 to be targeted with the light (a biofouling organism). The optical medium 5 generally extends in two dimensions significantly further than in the third dimension so that a two-dimensional-like object is provided. Optical structures 7 to scatter light 9 may be spread in one or more portions of the optical medium material, possibly throughout all of it, wherein in such portions the distribion may be generally homogeneous or localised. Scattering centres with different structural properties may be combined to provide, besides optical, also structural characteristics, such as resistance to wear and/or impact. Suitable scatterers comprise opaque objects but largely translucent objects may be used as well, e.g. small air bubbles, glass and/or silica; a requirement is merely that a change in refractive index occurs for the wavelength(s) used.

The principle of light guiding and spreading light over a surface is well-known and widely applied in various fields. Here, the principle is applied to UV light for the purpose of anti-fouling. It is noted that the idea of making a surface, e.g. the hull of a ship self-lit with UV is a clearly different solution than the current and well established anti-fouling solutions which rely on smooth coatings, chemicals, cleaning, software to control the ship speed, etc.

Total internal reflection is one way of transmitting light through an optical medium, which is then often referred to as a light guide. To maintain the conditions for total internal reflection, the index of refraction of the light guide should be higher than that of the surrounding medium. However, the use of (partly) reflecting coatings on the light guide and/or use of the reflective properties of the protected surface, e.g. the hull of a ship, itself can also be used to establish the conditions for guiding the light through the optical medium.

In some embodiments the optical medium may be positioned relative to the protected surface, e.g. the hull of a ship, such that a small air gap is introduced between the optical medium and the protected surface; UV light may travel even better—with less absorption—in air than in an optical medium, even when this optical medium is designed as a light guiding material. In other embodiments gas-filled channels, e.g. air channels, may be formed within silicone material. An array of separate gas-filled pockets may also be provided, e.g. in a regular pattern like a rectangular or honeycomb-pattern or in an irregular pattern. Instead of gas (e.g. air) filling, channels and/or pockets may be at least partly filled with a UV-transmissive liquid, e.g. fresh and/or purified water. In case a protected surface that is covered with such optical medium is subject to impact, e.g. a ship hitting a dockside, small pockets may soften, redistribute the impact energy and hence protect the surface, wherein liquid-filled pockets may be robuster under deformation than air-pockets which may more easily burst open.

As most materials have a (very) limited transmittance for UV light, care has to be taken in the design of the optical medium. A number of specific features and/or embodiments, which are dedicated for this purpose are listed in the following:

A relatively fine pitch of low power LEDs can be chosen, to minimize the distance light has to travel through the optical medium.

A 'hollow' structure can be used, e.g. a silicone rubber mat with spacers that keep it a small distance away from the protected surface. This creates air 'channels', through which the UV light can propagate with high efficiency (air is very transparent for UV). Use of gas filled channels provided by such structures allows distributing the UV light over significant distances in a optical medium of material that would otherwise absorb the UV light too strongly to be useful for anti-fouling. Similarly, separate pockets may be formed.

A special material can be chosen with high UV transparency, like certain silicones or UV grade (fused) silica. In embodiments, this special material can be used only for creating channels for the light to propagate the majority of the distance; a cheaper/more sturdy material can be used for the rest of the surface.

Further embodiments are disclosed in the accompanying drawings, wherein a main issue is to illuminate a large surface with anti-fouling light, preferably UV light, yet using point light sources. A typical concern is spreading of the light from point sources to surface illumination. In more detail:

The protected surface area of a typical container ship is ~10.000 m$^2$.

A typical LED source has an area of ~1 mm$^2$. This is 10$^{10}$ smaller.

Taking the required power levels into account, about 10 LEDs per m$^2$ may be required This means light has to be spread from 1 LED over ~1000 cm$^2$ As another boundary condition is taken that the solution should be thin (order of magnitude: 1 cm), e.g. for reasons such as:

To be able to add the solution as a 'coating' to a ship

To not increase drag due to an increased cross section size of the ship

To keep (bulk) material costs limited.

The use of an optical medium, in particular a generally planar light guide is therefore provided. Typical dimensions of a light guide are a thickness of about 1 mm to about 10 mm. In the other directions, there is no real limit to the size, from an optical point of view; in particular not if plural light sources are provided so that decay of light intensity throughout the light guide due to partial outcoupling of light and possibly (absorption) losses are countered.

Figure 8:
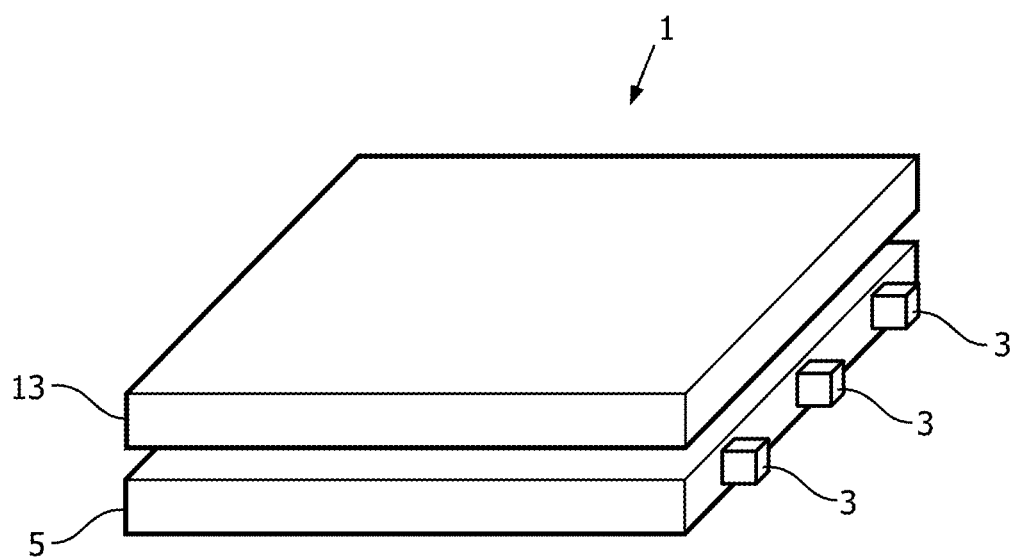
FIG. 8 shows a general concept of light guiding used in embodiments.
Figure 9A:
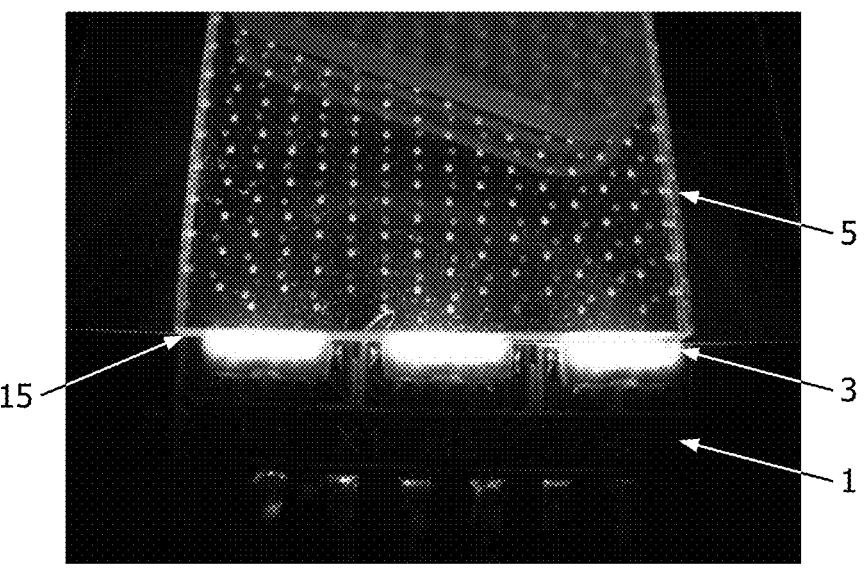
FIGS. 9(a)-9(b) show a realised planar light guide embodiment.
Figure 9B:
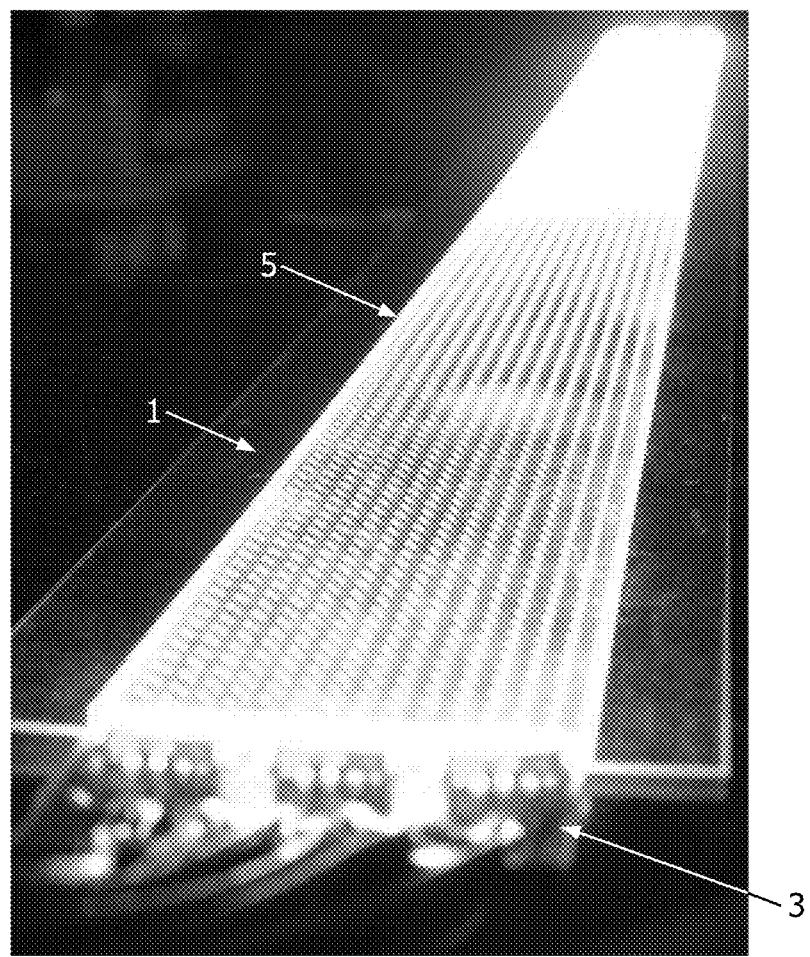

Here, it is considered that similar optical challenges apply as with the design of LCD TV backlights, although emission light intensity uniformity is less stringent in anti-fouling than with LCD TV backlights. FIG. 8 shows a lighting module 1 with light sources 3 and a light guide 5 with an additional top layer 13. FIGS. 9A-9B show practical examples of the principle illustrated in FIG. 8 and show a lighting module 1 with LED sources 3 which are positioned along the edge 15 of a light guide 5 and which inject light into the light guide 5. A pattern of scatterers e.g. white dots of paint, or small scratches/dents extract the light in appropriate places, here generally uniform (FIG. 9B), so that a desired, e.g. generally homogeneous, illumination distribution of the environment is achieved.

Figure 10A:
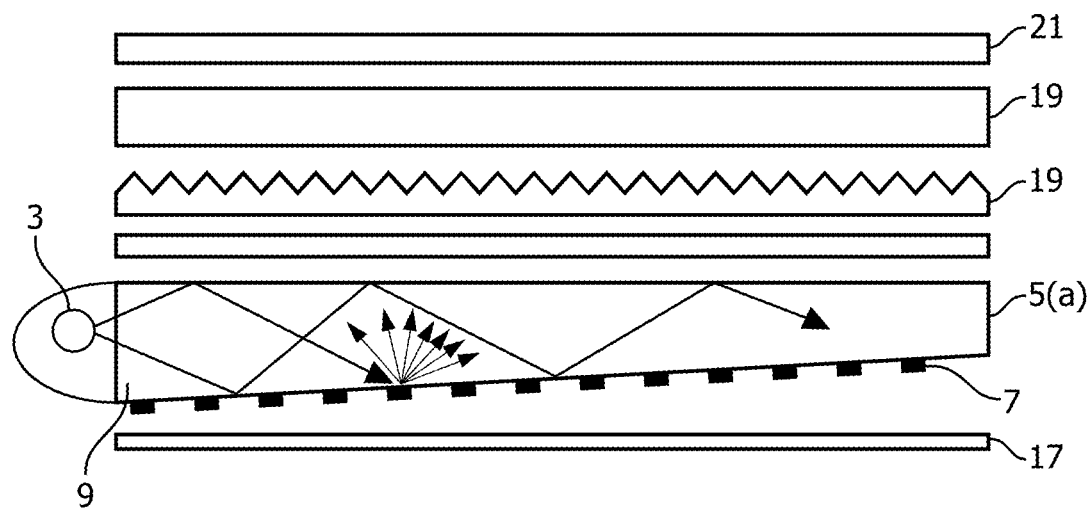
FIGS. 10(a)-10(b) show wedge shaped light guide embodiments.

FIG. 10(a) shows a LCD TV backlight arrangement wherein a wedge-shaped light guide 5(a) is employed wherein the light from a light source 3 is injected into the light guide 5(a) from the side. The light guide 5(a) is arranged with a pattern of scattering objects 7, such as dots of paint or scratches, on a reflective substrate 17. A wedge shape causes more of the light to be extracted towards the tip end. The prism sheets 19 and LCD panel 21 that orient polarisation states of the light and generate visible light colours are feature that can be omitted in an anti-fouling context.

Figure 10B:
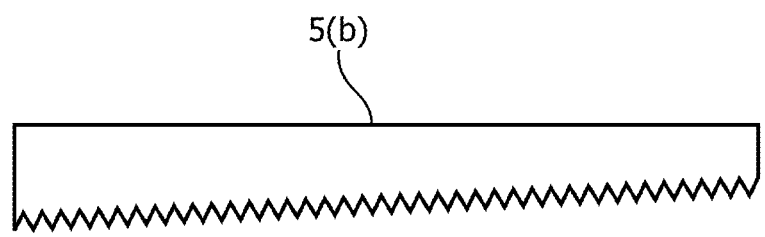

FIG. 10(b) shows another wedge shaped light guide 5(b) which is provided itself with a structured side so as to scatter and redistribute light within and out of the light guide 5(b).

Both the plane light guide and wedge-shaped light guide share the principle of guiding light along a substantial distance substantially parallel to the emission surface. The alternatives shown in FIG. 11a-11(b) (see below) are known as a direct-lit optical medium; here one or more LEDs and/or other light source(s) is present behind a screen e.g. a diffuser and emit light directly towards the object to be illuminated, e.g. a biofouling organism.

In a side-lit optical medium, often referred to as a light guide, such as those shown in FIG. 8-10(b) a side of the optical medium is illuminated from one or more light sources relatively strongly and further away from the light source(s) the light intensity within light guide is generally more homogeneous, possibly governed by scatterers (FIGS. 9(a)-9(b)).

In short, a difference beweem side-lit or direct-lit concepts is that in direct-lit situations the light travels no substantial distance parallel to the emission surface. As a result, the light intensity is usually much higher directly in front of the light sources. No real distribution of light is achieved. Thus, in a direct-lit solution a larger intensity variation may be expected between areas directly in front of the light source(s) and area aside thereof.

Figure 11A:
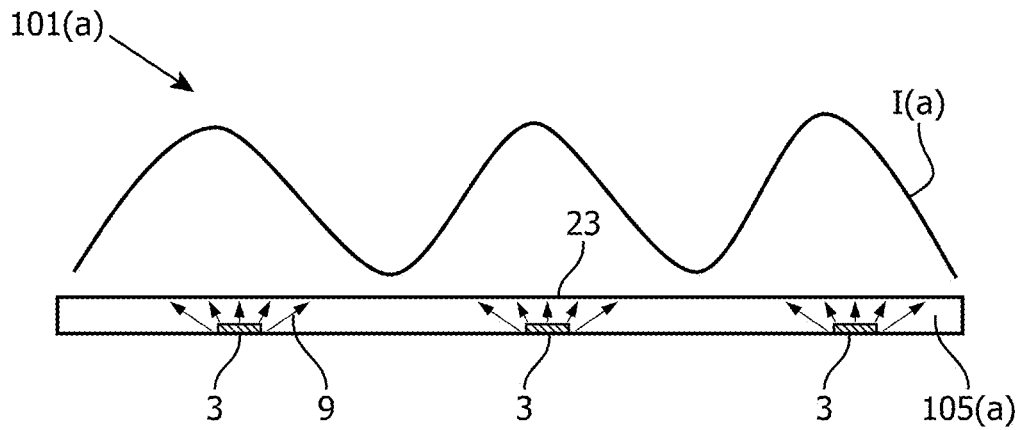
FIGS. 11(a)-11(b) show direct-lit light guide embodiments.
Figure 11B:
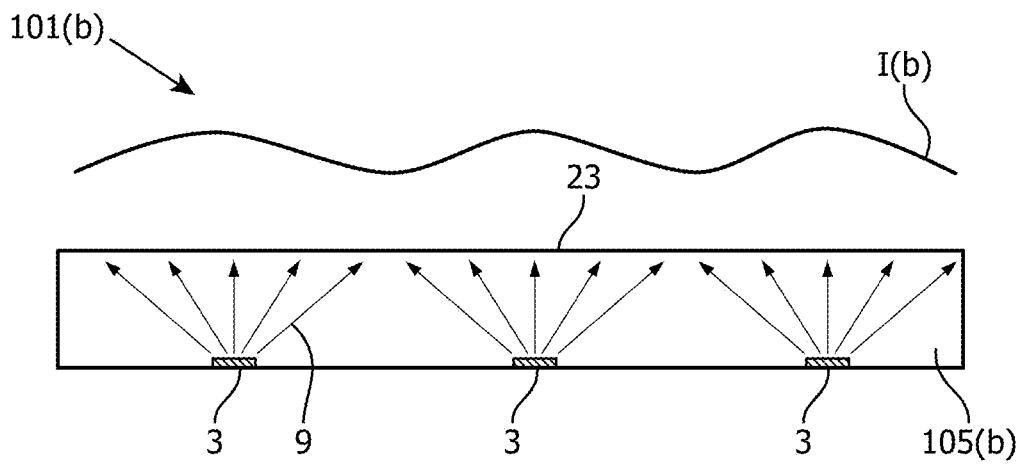

FIGS. 11(a) and 11(b) show lighting modules 101(a), 101(b) in cross section view (cf FIG. 7) comprising light sources 3 and optical medium 105(a), 105(b) having an emission surface 23. The wavy line "I(a)" and "I(b)", respectively, show the light intensity profile emitted from the emission surface and illustrate that a thicker optical medium 105(b) (FIG. 11(b)) will 'automatically' provide a better light uniformity on the emission surface 23 than a thinner optical medium 105(a) (FIG. 11(a)) of otherwise identical construction.

However, in the present case such relative intensity variations need not be of much concern. Further, direct lit arrangements potentially also have capability of controlling local intensity variations, which may also be utilised for providing both temporal and spatial intensity variations. Thus, the optical structure provided herewith is relatively simple. As a rule of thumb, for a high level of emission light intensity, the thickness of a optical medium in a direct-lit configuration is generally about equal to the LED pitch. If the LED pitch is 10 cm, this rule of thumb might lead to an optical medium that is about 10 cm thickness, which is thicker than desired. However, the light emission uniformity requirements for the presently intended purpose of anti-fouling do not have to meet 'substantially uniform lighting' requirements and hence a thinner layer may be used in combination with such LED pitch.

Additional ideas and solutions exist to obtain a better uniformity in a thinner optical structure, such as introduction of scatters and/or reflectors or other light spreaders directly in front of one or more light sources.

Figure 12:
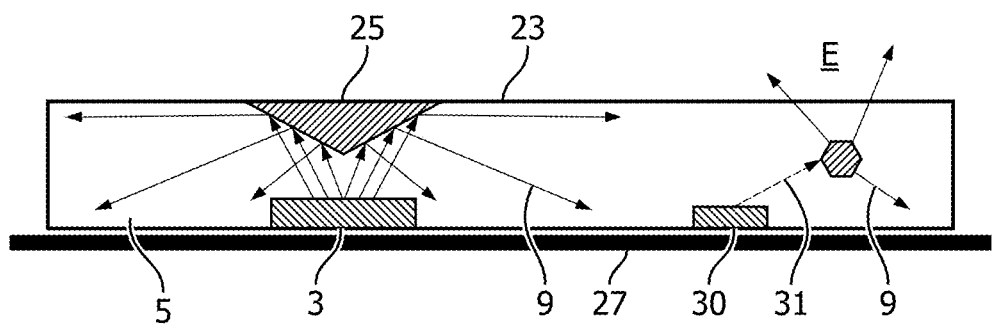
FIG. 12 shows an embodiment comprising a redistribution reflector and a wavelength conversion material.

FIG. 12 shows (left hand side) inclusion of a light spreader in the form of a reflective cone 25 in the optical medium 5 with an apex towards the light source 3. This directs the light 9 in a direction having a component substantially parallel to the surface 27 to be protected against fouling. If the cone 25 is not fully reflective nor opaque, some light from the light source will pass through it and creation of shadows leading to reduced or ineffective anti-fouling is prevented.

Further, FIG. 12 shows (right hand side) a wavelength conversion material which is comprised in the optical medium 5. The illustrated embodiment is configured to generate at least part of the anti-fouling light by photo-exciting the wavelength conversion material with light from a light source 30 with light 31 having a first wavelength causing the wavelength conversion material to emit anti-fouling light 9 at another wavelength from the optical medium 5 into the environment E. The distribution of wavelength conversion material in optical medium 5 may be spatially varying, e.g. in accordance with (expected) intensity distributions of (different wavelengths of) light in the optical medium 5.

Figure 13:
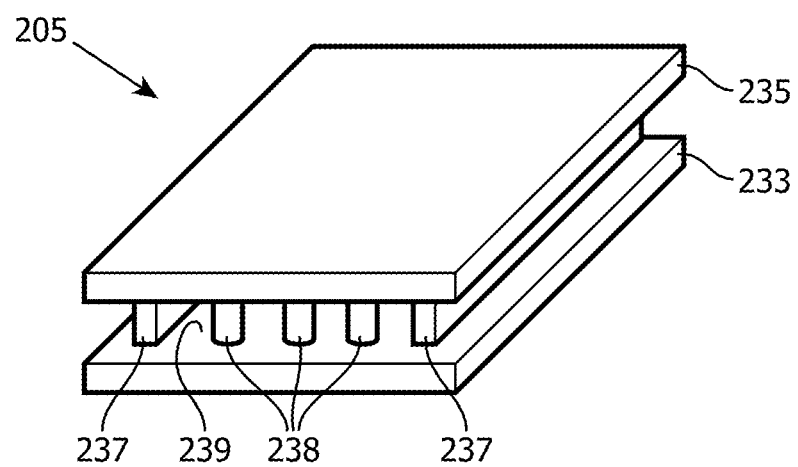
FIG. 13 shows a light guide comprising gas-filled channels.

FIG. 13 shows an optical medium 205 comprising a first layer 233, a second layer 235 with a plurality of walls 237 and pillars 238 in between separating the first and second layers 233, 235 and creating gas-filled channels 239. The optical medium 205 may be used just as any of the other optical mediums shown herein.

Figure 14:
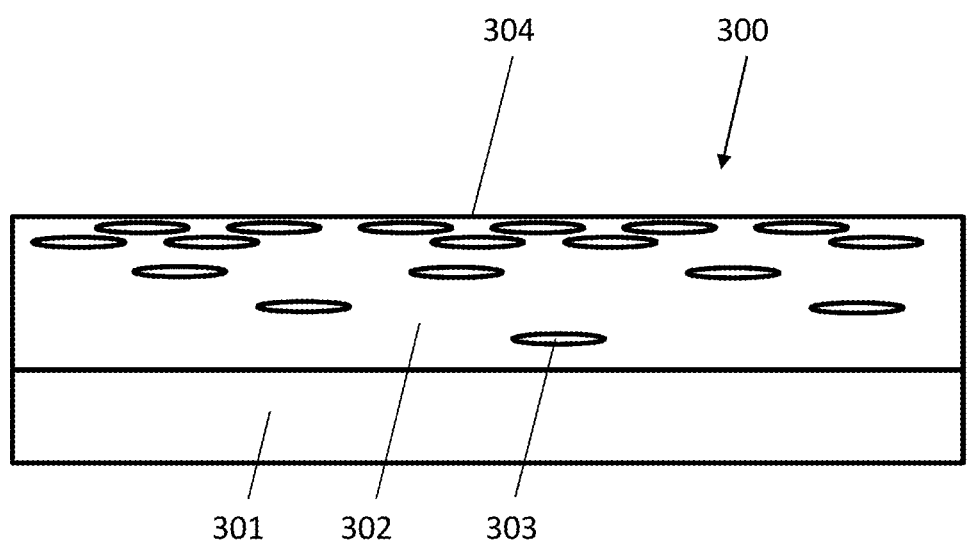
FIG. 14 shows an embodiment comprising distributed embedded flakes.

FIG. 14 shows a portion of an object 300 to be protected against biofouling, comprising an object surface 301, e.g. a ship hull, provided with an optical medium 302 comprising embedded flake-shaped particles 303. (In the drawing, the light sources are omitted.) The flakes 303 are distributed generally parallel to each other and with increasing density from the object surface 301 outwards to an emission surface 304.

Figure 15:
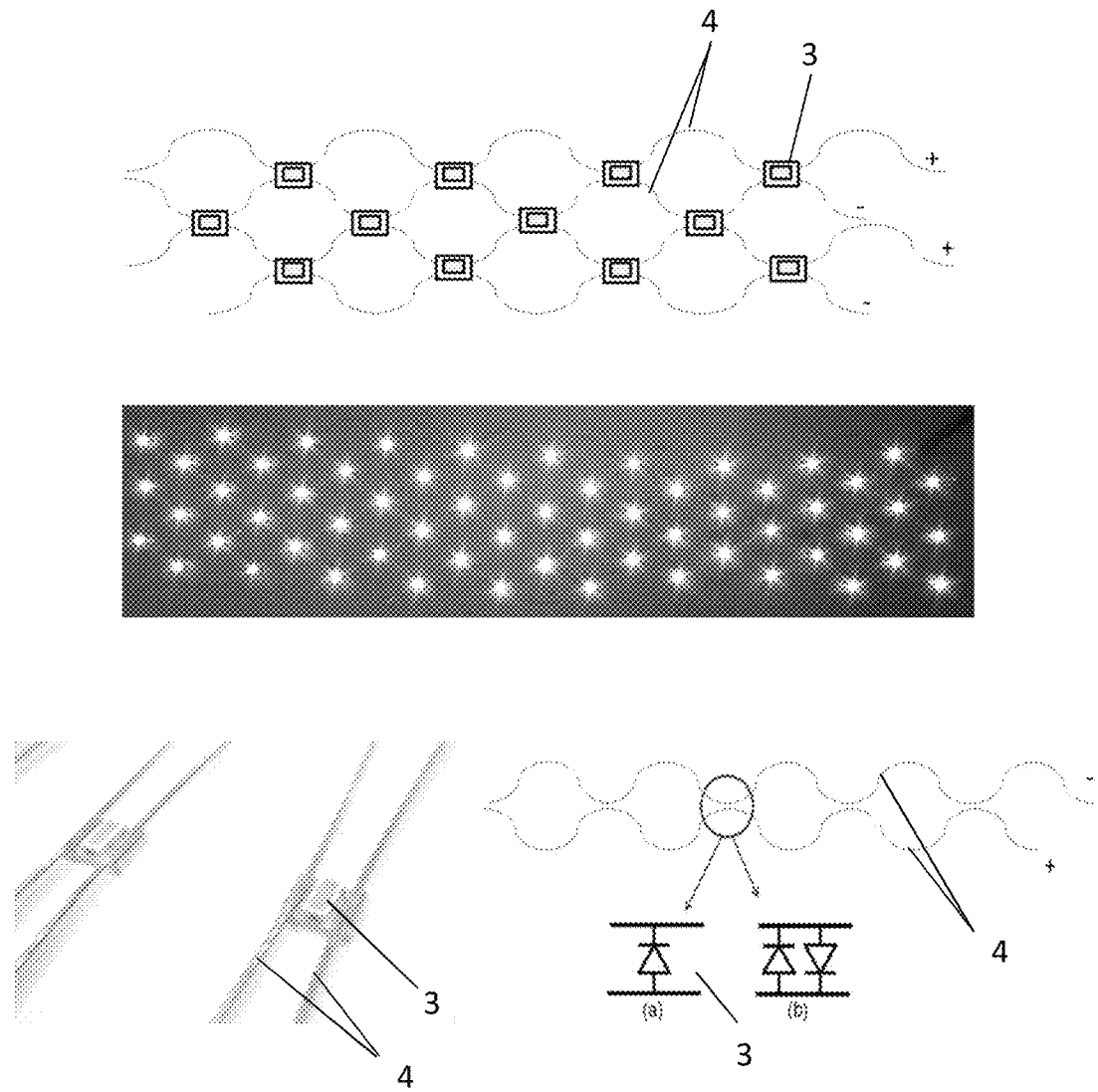
FIG. 15 shows an embodiment of a chicken-wire grid.

FIG. 15 shows a chicken-wire embodiment where UV LEDs 3 are arranged in a grid and connected in a series of parallel connections. The LEDs can be mounted at the nodes as shown in bottom left of FIG. 15 either through soldering, glueing or any other known electrical connection technique for connecting the LEDs to the chicken wires 4. One or more LEDs can be placed at each node. DC or AC driving can be implemented. In case of DC, the LEDs are mounted as shown at the bottom right (a) of FIG. 15. If AC is used, then a couple of LEDs in anti parallel configuration is used as shown at the bottom right (b) of FIG. 15. The person skilled in the art knows that at each node more than one couple of LEDs in anti parallel configuration can be used. The actual size of the chicken-wire grid and the distance between UV LEDs in the grid can be adjusted by stretching the harmonica structure. The chicken-wire grid may be embed in an optical medium wherein optionally a parallel grid of scattering features are provided as illustrated in FIG. 12.

Besides anti-fouling application of hulls of ships, the following alternative applications and embodiments are envisioned:

The disclosure can be applied to a wide variety of fields. Almost any object coming into contact with natural water, will over time be subject to biofouling. This can hinder e.g. water inlets of desalination plants, block pipes of pumping stations, or even cover the walls and bottom of an outdoor pool. All of these applications would benefit from the presently provided method, lighting modules and/or system, i.e. an effective thin additional surface layer, which prevents biofouling on the entire surface area.

Although UV light is the preferred solution, other wavelengths are envisaged as well. Non-UV light (visible light) is also effective against biofouling. Typical micro-organisms are less sensitive to non-UV light than to UV light, but a much higher dose can be generated in the visible spectrum per unit input power to the light sources.

UV LEDs are an ideal source for thin light emitting surfaces. However, UV sources other than LEDs can also be used, such as low pressure mercury vapour lamps. The form factor of these light sources are quite different; mainly the source is much bigger. This results in different optical designs, to 'distribute' all the light from a single source over a large area. The concept of light guiding as discussed herein does not change though. Further, a significant contribution of light in desired wavelengths and/or wavelength combinations may be produced.

Instead of using a thin layer that emits UV light outward in a direction away from the protected surface in order to avoid bio-fouling, biofouling could potentially also be removed by applying UV light from the outside in the direction of the protected surface. E.g. shining a UV light onto a hull or surface comprising a suitable optical medium as described. Thus, a single optical medium emitting anti-fouling light in directions to and away from protected surfaces may be even more efficient.

The concepts are not restricted to the above described embodiments which can be varied in a number of ways within the scope of the claims. For instance, using light, in particular UV light as an anti-biofouling means can provide an interesting opportunity in other fields. It is unique in the sense that continuous "24/7" 'protection' can be provided, over a large area. The application is especially interesting for the hull of ships, but can also be applied in swimming pools, water treatment plants, etc. Instead of water, biofouling may occur and be treated in other liquid environments, e.g. oils, brines and/or liquids in other environments including food industry.

Elements and aspects discussed for or in relation with a particular embodiment may be suitably combined with elements and aspects of other embodiments, unless explicitly stated otherwise.

What is claimed is:

1. A module for protecting a surface from fouling, the module comprising:
an optical medium in close proximity to the protected surface, comprising at least one light source extending into the optical medium, the at least one light source configured to generate a light,
wherein the optical medium comprises:
a first layer; and
a second layer,
wherein the first layer and the second layer are separated by a plurality of spacers,
wherein the spacers form at least one of spaces and pockets between the first layer and the second layer,
wherein at least one of the first layer and the second layer is configured to distribute at least part of the light through the optical medium,
wherein the light source is configured to direct the light substantially parallel to the protected surface;
an emission surface configured to emit anti-fowling light in a direction away from the protected surface, wherein the anti-fowling light depends on the light generated by the light source; and
a reflecting surface on an opposite side of the optical medium from the emission surface, wherein the light reflect from both the reflecting surface and the emission surface as the light travels through the medium substantially parallel to the protected surface,
wherein the optical medium and the emission surface are configured to be distributed over the protected surface.

2. The module of claim 1, wherein the emission surface comprises one of a transparent surface of the optical medium and a coating applied to a surface of the optical medium.

3. The module of claim 1, wherein the at least one of spaces and pockets are filled with one of a gas and a liquid.

4. The module of claim 3,
wherein the at least one of spaces and pockets are arranged in a pattern,
wherein the pattern in arranged to form at least one of a regular pattern and an irregular pattern.

5. The module of claim 4, wherein the regular pattern is one of a linear channel, a rectangular channel, and a honeycomb.

6. The module of claim 1, wherein the at least one light source is arranged in a two dimensional grid.

7. The module of claim 1, wherein a distance between two adjacent ones of the at least one light source is one of uniform, and variable.

8. The module of claim 1, wherein the emission surface is liquid tight.

9. The module of claim 1, wherein the optical medium comprises a material selected from a group comprising at least one of silicones and UV grade silica.

10. The module of claim 1, wherein the optical medium comprises a light spreader.

11. The module of claim 1, wherein the optical medium comprises a plurality of spatially distributed UV grade translucent particles.

12. The module of claim 11, wherein a density of the spatially distributed UV grade translucent particles increases from within the optical medium towards the emission surface.

13. The module of claim 1, wherein the at least one light source is at least one of a Light Emitting Diode (LED) and an Organic Light Emitting Diode (OLED).

14. The module of claim 1, wherein the lighting module is shaped as one of a tile, and an elongated strip.

15. The module of claim 1, wherein the light is one of a UV light and a visible light.

16. The module of claim 1,
wherein the optical medium comprises a wavelength conversion material,
wherein the wavelength conversion material is configured to convert the light generated at a first wavelength to a second wavelength,
wherein the second wavelength is in a UV range.

17. The module of claim 15, wherein the UV light is between 240 nm and 280 nm.

18. The module of claim 16, wherein the UV range is about 240 nm to about 280 nm.

19. The method of claim 13,
wherein the anti-fouling light is emitted from a plurality of light sources arranged in a two-dimensional grid,
wherein the anti-fouling light is emitted onto or in close proximity to the protected surface.

20. The module of claim 1,
wherein the emission surface is a substantially planar surface,
wherein the emission surface masks or obscures a thickness of the at least one light source and wiring connections embedded in the lighting module.

21. The module of claim 1,
wherein the emission surface is a substantially planar surface,
wherein the emission surface masks or obscures constructional unevenness of the protected surface.

22. The module of claim 1, wherein the at least one light source comprises at least one UV LED.

23. The module of claim 1,
wherein the optical medium comprises a silicone material selected from the group consisting of methyl-silicones, and/or UV grade silica material,
wherein the optical medium is selected from the group consisting of a light guide, a light spreader or a combination of a light guide and a light spreader.

24. The module of claim 1, wherein the layer of the optical medium is configured to distribute the generated light using internal reflection.

25. The module of claim 1,
wherein a wavelength conversion material is disposed in the optical medium,
wherein at least part of the anti-fouling light is generated by photo-exciting the wavelength conversion material with light having a first wavelength causing the wavelength conversion material to emit the anti-fouling light at another wavelength.

26. The module of claim 1, wherein a plurality of lighting modules are arranged on the protected surface so as to provide anti-fouling light over substantially the entire area of the protected surface.

27. A ship comprising at least one module according to claim 1.

28. The ship of to claim 27, wherein a hull is the protected surface.

29. A module for protecting a surface from fouling, comprising:
a medium, the medium arranged substantially planar to the protected surface, in close proximity with the protected surface, comprising:
a first layer;
a second layer; and
a plurality of walls separating the first layer and the second layer, the plurality of walls forming a plurality of channels between the first layer and the second layer; and
a plurality of light sources arranged with respect to the plurality of channels,
wherein the plurality of light source are arrange to generate anti-fowling light,
wherein the channels are configured to distribute the light generated by the plurality of light sources,
wherein the light is directed substantially parallel to the protected surface and then directed away from the protected surface.

30. The system of claim 29, wherein the channels are filled with one of a gas and a liquid.

31. The module of claims 29, wherein the channels comprise a material selected from a group comprising at least one of silicones and UV grade silica.

32. The module of claim 29, wherein the medium is arranged in one of a tile and an elongated strip.

33. The module of claim 29, wherein a distance between neighboring light sources is one of uniform and variable.

34. The module of claim 33, wherein the distance between neighboring light sources is based on a desired light output power.

35. The module of claim 29, wherein the plurality of light sources are arranged in one of a foil and an electronic textile.

36. The module of claim 29, wherein the two dimensional grid is arrange in one of a chicken-wire structure, a close-packed structure, a rows/columns structure, a regular structure and an irregular structure.

37. The module of claim 29, further comprising a plurality of spatially distributed UV grade translucent particles embedded within the channels.

38. The module of claim 37, wherein a density of the spatially distributed UV grade translucent particles increases from within the first layer to the second layer.

39. The module of claim 29, wherein the plurality of light sources are selected from a group consisting of a Light Emitting Diode (LED) and an Organic Light Emitting Diode (OLED).

40. The module of claim 29, wherein the generated light is one of a UV light in a wavelength range of 240 nm to 280 nm.

41. A system configured to protect a surface subjected to bio-fouling, the system comprising:
at least one module, the at least on module configured to be positioned proximate a surface to protect the surface from bio-fowling, the at least one module comprising:
at least one light emitting diode contained within a liquid tight encapsulation, the at least one light emitting diode configured to generate a light; and
a medium comprising:
a layer distributing at least part of the generated light to increase the homogeneously of the light through the medium; and
a plurality of optically transparent channels,
wherein an emission surface of the medium is configured to emit the light through the emission surface away from the protected surface.

42. The system of claim 41, wherein the at least one module is arranged in one of a tile and an elongated strip.

43. The system of claim 41 wherein the at least one light emitting diode is configured to generate the light in a UV wavelength range.

44. The system of claim 41, wherein the at least one light emitting diode is configured to generate the light in a visible wavelength range.

45. The system of claim 44, the medium comprises a wavelength conversion material configured to convert the visible wavelength light into a UV wavelength of light.

46. The system of claim 41, wherein the medium is optically transparent.

47. The system of claim 41, wherein the medium comprises a plurality of layers having one of different composition and particle density.

48. The system of claim 47, wherein the plurality of layers may be one of formed and sprayed on a prior layer.

49. The system of claim 41, wherein the emission surface comprises one of a surface of the optical medium and a coating applied to a surface of the optical medium.

50. The system of claim 41, further comprising a light spreader positioned opposite a corresponding one of the plurality of light emitting diode.

51. The system of claim 41, wherein the plurality of light emitting diodes are contained within the medium.

52. The system of claim 41, wherein the plurality of light emitting diodes are positioned on the medium.

53. The system of claim 41, the medium comprising a plurality of scatterers, the scatterers selected from the group consisting of air bubbles, imperfections, silica, glass, mica and combinations thereof.

54. The system of claim 53, wherein the plurality of scatterers distribute the light at least one of away from the surface and toward the surface.

55. The system of claim 53,
wherein the scatterers comprise a spatially varying density of particles of UV translucent particles, UV grade silica particles,
wherein the scatterers are at least partly embedded in a silicone material, and
wherein the density of the UV grade silica particles in the silicone material increases from within the optical medium towards the emission surface of the optical medium in at least part of the optical medium.

56. The system of claim 41, wherein the surface subjected to bio-fouling is configured to be submersible.

57. The system of claim 41, wherein a distance between neighboring light sources is one of uniform and variable.

58. A foil, configured to protect a surface from bio-fouling, the foil comprising:
a plurality of light sources, wherein the plurality of light sources are configured to generate a light in at wavelength band comprising at least one of a visible light band and a UV light band; and
an optical medium comprising:
a layer with a first surface and a second surface; and
a plurality of channels,
wherein the first surface is an emission surface for passing light away from the medium, conforming to a protected surface to be protected from bio-fouling,
wherein the optical medium is configured to receive the generated light,
wherein the optical medium is configured to distribute, within the layer of the optical medium, the light in a direction substantially parallel to the protected surface; and
a plurality of imperfections, within the optical medium, directing portions of the light to be emitted from the emission surface away from the optical medium.

59. The foil of claim 58, wherein the optical medium comprises an emission layer.

60. The foil of claim 58, wherein the emission layer is one of a layer of the optical medium, and a coating on the optical medium.

61. The foil of claim 58, wherein the foil is configured as one of sized limited in two orthogonal directions perpendicular to a thickness of the foil and size limited in only one direction perpendicular to a thickness of the foil.

62. The foil of claim 58, wherein the foil is configured to be placed on or proximate to the surface.

63. The foil of claim 59, wherein the emission layer is substantially planar.

64. The foil of claim 58, wherein the plurality of light sources are configured in one of a chicken-wire pattern, a close-packed pattern, a rows/columns pattern, a regular pattern and an irregular pattern.

65. The foil of claim 58, wherein the plurality of light sources are arranged within the optical medium.

66. The foil of claim 58, wherein the plurality of light sources are arranged on a surface of the optical medium.

67. The foil of claim 58, wherein the optical medium is transparent to the light.

68. The foil of claim 58, wherein the channels are transparent to the light.

69. The foil of claim 58, wherein the channels are filled with at least one of a gas and a liquid.

70. The foil of claim 58, wherein the plurality of light emitting diodes are contained in a liquid tight encapsulation.

71. The foil of claim 58, wherein the plurality of imperfections are selected from a group consisting of air bubbles, scratches, indentations, silica, glass and mica.

72. The foil of claim 58, wherein the surface is configured to be submersed in a liquid.

73. The foil of claim 58, wherein the surface is subject to bio-fouling.

74. The foil of claim 58, wherein the optical medium is one of a material comprising silicon and a silica.

75. The foil of claim 73, wherein the optical medium wherein a reflective index of the imperfections is different than a reflective index of the optical medium.

76. The foil of claim 58, wherein the channels are comprised of one of a material comprising silicon and a silica.

77. The foil of claim 76, wherein the channels comprises a plurality of imperfections wherein a reflective index of the imperfections is different than a reflective index of the channel.

78. The foil of claim 58, wherein a distance between neighboring light sources is one of uniform and variable.

79. A foil, configured to protect a surface from biofouling, the foil comprising:
a plurality of light sources configured to generate a light in at wavelength band, wherein the wavelength band is selected from the group consisting of a visible light band and a UV light band; and
an optical medium comprising:
a layer within which the light sources extend;
a plurality of channels,
wherein the channels comprise one of air, a liquid, a material comprising silicon, and a silica,
wherein the channels comprise a plurality of regions,
wherein a reflective index of the plurality of regions is different than a reflective index of the channel,
wherein the light is output at the plurality of regions
wherein the optical medium is configured to receive the generated light,
wherein the optical medium is configured to distribute, within the layer of the optical medium, the light in a direction substantially parallel to the optical medium,
wherein the optical medium is configured to selectively output portions of the light through an emission surface of the layer, in a direction substantially perpendicular to the distributed direction of light.

80. The foil of claim 79, wherein the optical medium is one of a material comprising silicon and a silica.

81. The foil of claim 80,
wherein the optical medium comprises a plurality of regions,
wherein a reflective index of the regions is different than a reflective index of the optical medium,
wherein the light is output at the plurality of regions.

82. The foil of claim 79, wherein a distance between neighboring light sources is one of uniform and variable.

83. A method of anti-fouling of a protected surface, comprising:
providing an anti-fouling light;
providing an optical medium in close proximity to the protected surface, the optical medium having an emission surface;
distributing at least part of the anti-fouling light through the optical medium in a direction substantially parallel to the protected surface;
emitting the anti-fouling light from the emission surface of the optical medium in a direction away from the protected surface; and
distributing at least part of the anti-fouling light through spaces in the optical medium,
wherein the spaces are filled with gas and/or clear liquid comprising water,
wherein the anti-fouling light is emitted by at least one light source embedded in the optical medium,
wherein the protected surface is at least partially submersed in a liquid.

84. The method of claim 83,
wherein the emission surface is a substantially planar surface,
wherein the emission surface masks or obscures a thickness of the at least one light source and wiring connections embedded in a lighting module.

85. The method of claim 83,
wherein the emission surface is a substantially planar surface,
wherein the emission surface masks or obscures constructional unevenness of the protected surface.

86. The method of claim 83, wherein the at least one light source comprises at least one UV LED.

87. The method of claim 83,
wherein a wavelength conversion material is disposed in the optical medium,
wherein at least part of the anti-fouling light is generated by photo-exciting the wavelength conversion material with light having a first wavelength causing the wavelength conversion material to emit the anti-fouling light at another wavelength.

88. The method of claim 83,
wherein the optical medium comprises a silicone material selected from the group consisting of methyl-silicones, and/or UV grade silica material,
wherein the optical medium is selected from the group consisting of a light guide, a light spreader or a combination of a light guide and a light spreader.

89. The method of claim 83, further comprising:
providing at least a part of the optical medium with a spatially varying density of UV translucent particles, wherein the UV translucent particle are at least partly embedded in a silicone material; and
emitting the anti-fouling light from an emission surface of the optical medium, wherein in part of the optical medium the density of the UV grade silica particles in the silicone material increases from within the optical medium towards the emission surface of the optical medium.

90. The method of claim 83, wherein a plurality of lighting modules are arranged on the protected surface so as to provide anti-fouling light over substantially the entire area of the protected surface.

* * * * *